United States Patent [19]

Jeffcoat et al.

[11] Patent Number: 4,764,114
[45] Date of Patent: Aug. 16, 1988

[54] ANALYSIS SYSTEM

[75] Inventors: Robert L. Jeffcoat, Bedford; Khushroo M. Captain, Cambridge; Brian J. Doherty, Marblehead, all of Mass.

[73] Assignee: Foster-Miller, Inc., Waltham, Mass.

[21] Appl. No.: 818,484

[22] Filed: Jan. 13, 1986

[51] Int. Cl.⁴ ............................................. A61C 19/04
[52] U.S. Cl. ..................................... 433/72; 433/120; 128/776; 33/514
[58] Field of Search ................. 433/32, 120, 124, 118, 433/72, 115; 128/776, 777, 739, 740; 33/514

[56] References Cited

U.S. PATENT DOCUMENTS

| | | | |
|---|---|---|---|
| 1,327,114 | 1/1920 | Rhein | 33/169 R |
| 3,058,225 | 10/1962 | Ward | 128/776 |
| 3,239,938 | 3/1966 | Kaercher | 33/172 E |
| 3,559,292 | 2/1971 | Weissman | 433/72 |
| 3,660,901 | 5/1972 | Inoue | 433/75 |
| 3,943,914 | 3/1976 | Grenfell | 433/32 |
| 4,215,698 | 8/1980 | Nuwayser | 128/776 |
| 4,250,985 | 2/1981 | Lees | 192/48.7 |
| 4,470,810 | 9/1984 | Bourdeau et al. | 433/72 |
| 4,485,823 | 12/1984 | Yamagu | 128/776 |
| 4,499,906 | 2/1985 | Wohlgemuth et al. | 128/776 |
| 4,570,632 | 2/1986 | Woods | 433/118 |

OTHER PUBLICATIONS

Van der Velden, U. (1978), "Errors in the Assessment of Pocket Depth in Vitro", Journal of Clinical Periodontology 5, 182,187.
Van der Velden, U. & DeVries (1978), "Introduction of a New Periodontal Probe: The Pressure Probe", Journal of Clinical Periodontology 5, 188,197.
Vitek, R. M., Robinson, P. J. & Lautenschlager, E. P. (1979), "Development of a Force-Controlled Periodontal Probing Instrument", Journal of Periodontal Research 14, 93-94.
Van der Velden (1980), "Influence of Periodontal Health on Probing Depth and Bleeding Tendency", Journal of Clinical Periodontology 7, 129-139.

Primary Examiner—John J. Wilson

[57] ABSTRACT

Periodontal analysis apparatus includes a probe member having a tip, a probe housing having a guide channel in which the probe member is disposed for reciprocating movement with the tip of the probe member extending from the channel, force applying means for reciprocating the probe member in the housing, and transducer means in the housing for monitoring motion of the probe member and sensing perturbations in probe motion caused by the CEJ and providing output signals indicative thereof.

30 Claims, 3 Drawing Sheets

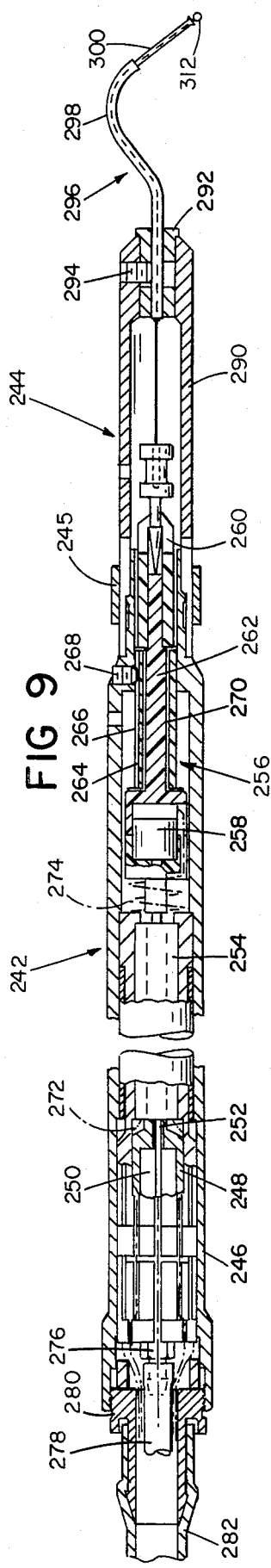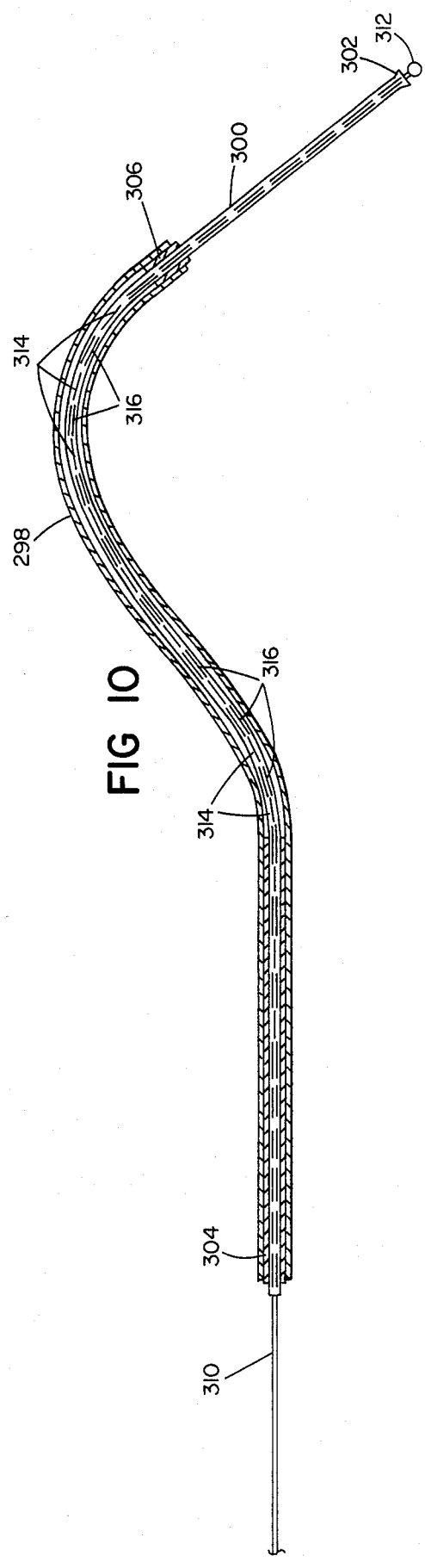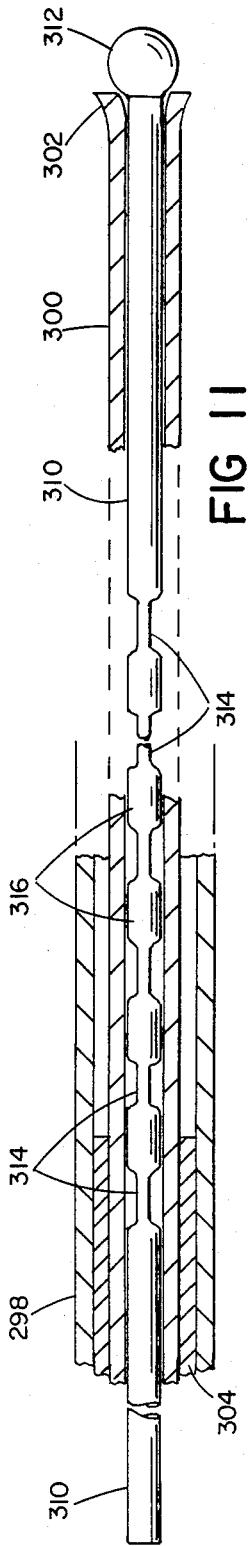

ANALYSIS SYSTEM

This invention relates to analysis apparatus and more particularly to periodontal analysis apparatus of the probe type.

The periodontal probe is a widely used diagnostic tool in the practice of periodontics, and is routinely used to measure the depth of the periodontal pocket (the distance from the gingival margin to the bottom of the clinical pocket). This measurement is relatively simple to make but suffers from the lack of a stable reference point. The position of the gingival margin may vary with changes in gingival inflammation, hypertrophy, or recession, which may in turn be independent of actual attachment loss. Loss of attachment, which may also be measured with a periodontal probe, is of greater importance from a pathophysiological point of view. Attachment level refers to the distance from the cemento enamel junction (CEJ) to the bottom of the clinical pocket. In contrast to pocket depth, this measurement is not affected by gingival inflamation or recession. In clinical practice, it is desirable to assess loss of attachment during the periodontal examination and following periodontal therapy. In research, the prevalence of loss of attachment has been assessed in epidemiological studies, as well as in longitudinal studies of the treatment and progression of periodontal disease. Two measurements are needed with the traditional probe to determine attachment level, as distinguished from pocket depth, a measurement of the distance from CEJ to the gingival margin and a measurement of the distance from gingival margin to pocket base.

The need for a noninvasive instrument that will quickly and accurately assess attachment level is widely felt, both in research and in clinical practice, as an aid to the early detection and close observation of disease. Such an instrument would desirably control or monitor the applied probing force, and permit high readout resolution, along with providing operator convenience, speed, and display and recording capabilities, and would aid in diagnosis of periodontal disease by means of more accurate and repeatable measurement of attachment level relative to CEJ.

In accordance with the invention, there is provided periodontal analysis apparatus that includes a probe member having a tip, a probe housing having a guide channel in which the probe member is disposed for reciprocating movement with the tip of the probe member extending from the channel, force applying means for reciprocating the probe member in the housing, and transducer means in the housing for monitoring motion of the probe member and sensing perturbations in probe motion caused by the CEJ and providing output signals indicative thereof.

In preferred embodiments, the probe member is housed in a sterilizable tip component that defines a guide channel of contra angle configuration and is detachable from a handle component that houses the transducer means; in a particular embodiment, the channel defining tip unit is a metal tube that has a flared end adjacent the tip of the probe member. In preferred embodiments, an elongated flexible probe member disposed in the guide channel has an enlarged or offset portion at its tip and a coupling portion at its end remote from the tip. In one particular embodiment, the probe member includes an elongated flexible assembly that includes a probe tip member, a coupling member, an elongated spring coil, and a tensioned filament extending through the spring coil from the probe tip member to the coupling member; while in another particular embodiment, the probe member is an elongated continuous metal wire member that has a diameter of less than 0.5 millimeter, a reduced diameter portion intermediate its ends, and an enlarged spherical tip.

The force applying means in those embodiments may include a bellows or a piston (which may be single acting or double acting) and a drive rod housed in the handle component, the drive rod being mechanically engaged with the probe member coupling portion and generating a probe tip insertion force of less than one hundred grams, a somewhat lower probe tip retraction force, and a probe tip displacement range of about one centimeter with a probe tip insertion retraction cycle of less than one second. A processor is responsive to the output signals of the transducer means, and output means responsive to the processor provides data on probe force, probe displacement and CEJ location.

Particular periodontal probes are designed to provide constant force probe movement with readout of both probe displacement and motion perturbations. Probe displacement in those embodiments is measured by an LVDT (linear variable differential transformer) which makes a direct measurement of probe tip displacement over the range of zero to twelve millimeters and probe motion perturbations are sensed with a piezoelectric accelerometer. The periodontal probe tip displacement force is applied via a low friction piston that is connected to the probe tip assembly by means of a rigid shaft which passes through the LVDT (the LVDT core being part of the shaft so that shaft motion gives a direct indication of probe tip displacement) and is coupled to the accelerometer. An optional supplemental channel supplies low pressure air to the tip of the guide channel.

In one particular embodiment, the tip of the drive shaft contacts a detent in a spring loaded plate which is attached to the flexible probe, the spring serving to retract the tip to its "reference" position at the end of the guide tube. A captured stainless steel spring wire that travels a small fraction of its free length, exerts approximately fifteen grams of retraction force at the probe tip and provides almost constant retraction force over its travel range. A probe tip insertion force of fifty grams maximum is obtained with a 0.6 centimeter diameter piston and a precisely regulated source of air at a pressure of two-hundred thirty grams per square centimeter (3.27 psi). In other particular embodiments, the drive assembly carries a coupling socket which receives the coupling end of the flexible probe, and a piston assembly both advances and retracts the probe tip (with the use of appropriate technology such as double acting cylinder or reduced pressure) so that essentially constant insertion and retraction forces of similar magnitudes are applied over the travel range of the probe tip. The insertion motion locates the base of the pocket, and the CEJ of the tooth under analysis produces a probe tip motion perturbation which provides an indication of attachment level. In one particular embodiment, the channel defining tip unit is a metal tube that has a flared end adjacent the tip of the probe member which may be used to manually locate the cemento-enamal junction.

Various transducer devices and related processing means may be used for probe displacement and motion perturbation measurement such as variable inductance and variable reluctance devices, resistance potientometers, optical and electro-optical devices, accelerometers and differential transformers (which are excited with high frequency, low voltage sinusoidal signals and have outputs proportional to the location of a metal core within the transformer). The probe may be oriented manually by holding the probe while resting one finger against a nearby tooth for reference; it may be also be located with stent, and with stereotaxic fixtures. Visual and audible responses can be provided in either analog or digital format with indications of both probe extension (pocket depth) and CEJ location. The invention provides accurate and repeatable measurement of attachment level relative to CEJ.

Other features and advantages of the invention will be seen as the following description of particular embodiments progresses, in conjunction with the drawings, in which:

FIG. 9 is a sectional view of another probe component embodiment;

FIG. 10 is an enlarged sectional view of the tip unit 296 of the probe component shown in FIG. 9; and FIG. 11 is a further enlarged sectional view of portions of the tip unit shown in FIG. 10.

DESCRIPTION OF PARTICULAR EMBODIMENTS

Figure 1:
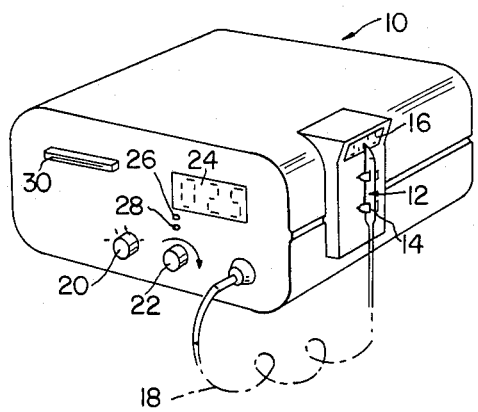
FIG. 1 is a perspective view of periodontal analysis apparatus in accordance with the invention.

The periodontal analysis apparatus shown in FIG. 1 includes console 10 with probe 12 secured by clips 14 for storage with its tip adjacent displacement/calibration pad 16. Probe 12 is connected via cable 18 to console 10 which houses air pressure sources and data processing equipment. Control knob 20 is movable between off, standby, calibration and automatic positions; and knob 22 permits adjustment of probe force. Display 24 displays output data—probe force in grams when selector 26 is depressed and probe extension (pocket depth) and attachment level in millimeters when selector 28 is depressed. Output slot 30 provides hard copy (printer) data.

Figure 2:
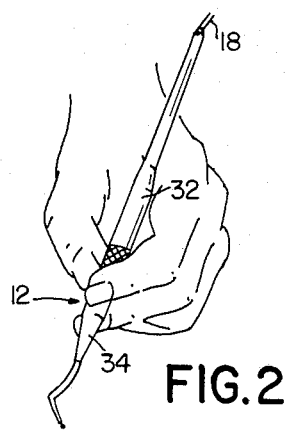
FIG. 2 is a perspective view of the probe component of the apparatus shown in FIG. 1.
Figure 3:
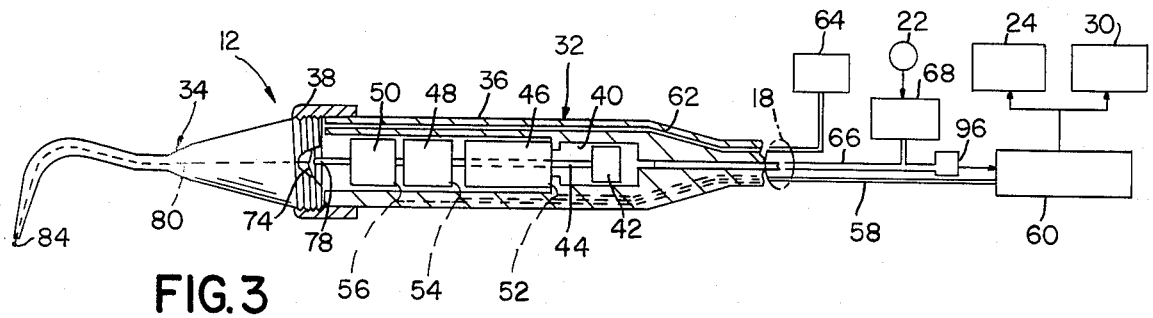
FIG. 3 is a diagrammatic and sectional view of the analysis system.

As indicated in FIG. 2, probe 12 is hand held and includes reusable hand piece unit 32 that is connected to cable 18 and detachable tip unit 34. Further details of probe 12 may be seen with reference to FIGS. 3 and 4. Hand piece 32 includes housing 36 with knurled threaded coupling 38 by which replaceable tip unit 34 is secured to hand piece 32. Formed within housing 36 is cylinder chamber 40 in which 0.6 centimeter diameter Teflon piston 42 is mounted for reciprocating movement. Rigid piston shaft 44 extends from piston 42 through linear variable differential transformer (LVDT) 46 (Schaevitz Engineering Model 250-MHR) to Piezoelectric force transducer 48 (Kistler Model 9712) and piezoelectric accelerometer 50 (Kistler Model 8616). Shaft 44 carries the core of LVDT 46 so that a direct indication of motion of shaft 44 is provided over LVDT output wires 52 via cable 18 to analysis circuitry 60 housed in console 10, and force transducer 48 and accelerometer 50 similarly apply output signals over lines 54 and 56 respectively. An optional air channel 62 in housing 36 is connected to a source of low pressure air 64. Piston 42 is connected via line 66 to source 68 of double regulated air pressure, the presure of which is adjusted by control 22. Air from source 68 at a pressure of two-hundred thirty grams per square centimeter generates a maximum probe tip insertion force of fifty grams.

Figure 4:
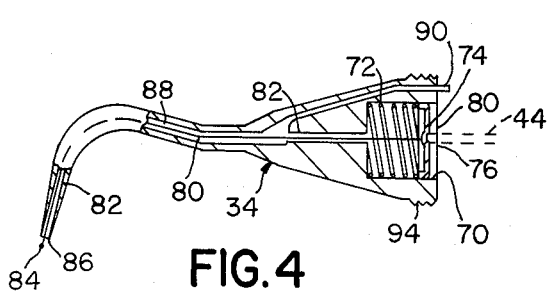
FIG. 4 is an enlarged sectional view of the tip unit of the probe component detached from the handle unit.

The detachable probe tip unit 34 is designed for easy removal for cleaning and autoclaving. As shown in FIG. 4, tip unit 34 includes chamber 70 which houses captive spring 72 is made from 0.015 millimeter diameter stainless steel wire, and has a free length of approximately fifteen centimeters. Plate 74 is carried by spring 72 and has a depression 76 which receives the tip 78 of piston shaft 44. Connected to plate 74 is an elongated flexible stainless steel probe member 80 which may be solid wire or braided cable and may be Teflon coated. Probe member 80 is rigid and straight in compression but bends easily around small radii when subjected to side forces. Probe member 80 extends through curved guide channel 82 and has enlarged tip 84. Formed in channel 82 is optional air passage 88 that communicates with coupling 90 which is received in a socket in handle unit 32 for connection to supply conduit 62. Tip unit 34 has threaded section 94 which cooperate with threaded coupling 38 to seat tip unit 34 against the end surface of hand piece unit 32. In that condition, coupling 90 is in its housing socket and tip 78 of piston rod 44 is seated in detent 76 of spring plate 74. Spring 72 exerts approximately fifteen grams of retraction force on probe tip 84, and urges piston 42 towards the remote end of chamber 40 and retracts probe wire 80 so that its tip 84 is closely adjacent the end 86 of probe channel 82.

While probe 12 is the basic instrument for data acquisition, control console 10 provides probe force control via double regulated air supply 68 and control 22; a probe force limit signal is provided by transducer 96 connected to the pneumatic probe supply line 66; and automatic calibration of the probe tip force is provided via calibration pad 16 so that the digital display 24 and recorder printer 30 automatically display the correct calibrated force at the probe tip 84, the force transducer in the calibration pad 16 being a strain gage bridge. Optional alarm and cutoff devices may be included in the system to avoid operation at excess pressure.

Figure 5:
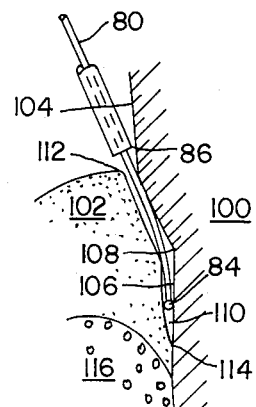
FIG. 5 is a schematic diagram showing the probe tip in proximity to a tooth.

FIG. 5 is a diagram of periodontal anatomy of tooth 100 and gingiva 102. Tooth 100 has an upper enamel surface 104 and a lower cementum surface 106 with cemento enamel junction 108. Pocket 110 extends along the tooth from the gingival margin 112 past the cemento enamel junction 108 to the pocket base 114 adjacent the point of attachment of the tooth to the periodontal ligament 116.

In use, the probe 12 is positioned with tip 84 at the gingival margin 112 and air pressure is applied to piston 42 (for example in response to a remote foot operated control) to advance probe tip 84 into pocket 110 to the base 114 of the pocket 110. The travel of the probe tip 84 is monitored by transducers 46, 48 and 50 and their outputs over lines 52, 54 and 56 to processor 60 provide a direct measurement of probe tip displacement, and displacement perturbations.

Concurrently, low pressure air from source 64 may be applied through channels 60 and 90 to the probe tip 84 to gently free the gingiva 102 from the tooth 100.

Figure 6:
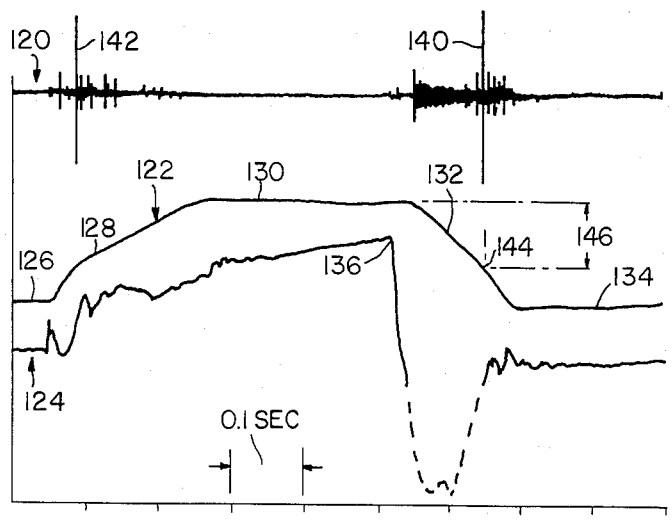
FIG. 6 is an oscillograph showing use of the probe to locate the cemento-enamel junction and to determine attachment level.

The oscilligraph of FIG. 6 shows an accelerometer trace 120 (produced by the transducer output on line 56), a probe tip displacement trace 122 (produced by the transducer output on line 52), and an applied force trace 124 (produced by the transducer output on line 54). Probe displacement trace 122 indicates motion of the probe tip 84 from its retracted position (at 126), advancing (at 128) along the enamel and cementum surfaces 104, 106 to the base 114 of pocket 110 (at 130), and then retracting (at 132) to the fully retracted position (at 134). As indicated by trace 124, the applied force increases and then the pressure in chamber 40 is vented (at 136), allowing spring 72 to return probe tip 84 and piston 42 rearwardly (as indicated by portion 132 of trace 122). As the tip 84 of flexible probe 80 retracts along cementum surface 106, a discontinuity is sensed by accelerometer 50 and produces the probe trace perturbation at 140 that indicates that discontinuity. That discontinuity is coincident with the location of cemento enamel junction 108. It will be noted that a similar acceleration perturbation 142 occurred as tip 84 advanced, but the acceleration perturbation 140 produced on the return is less ambiguous. As the maximum probe displacement 130 indicates the base of pocket 110 and the CEJ 108 is located on trace 122 at 144, attachment level (the distance 146 from the base of pocket 110 from CEJ 108) may be indicated directly, for example by recording the probe displacement position (point 144) at acceleration perturbation 140 and subtracting probe displacement value 130 (pocket depth) from probe displacement value 144 (CEJ). The resulting difference value may be shown at display 24 and/or provided as a hard copy printout at output 30.

Figure 7:
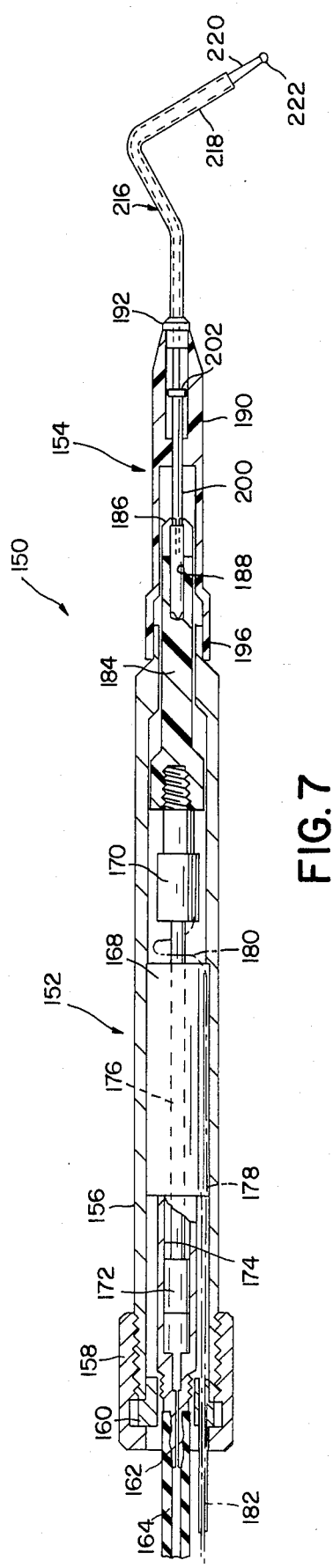
FIG. 7 is a sectional view of another probe component embodiment.
Figure 8:
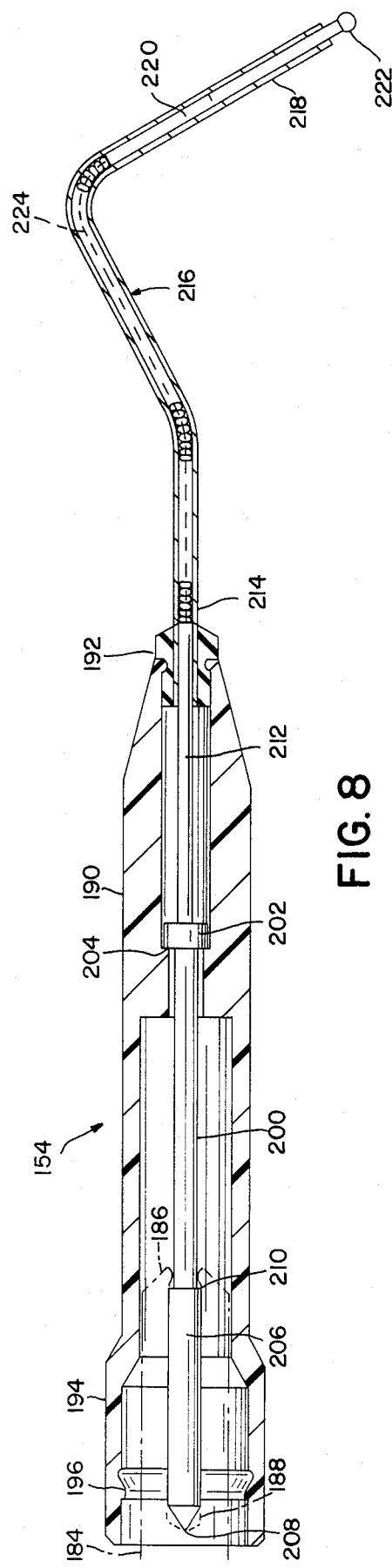
FIG. 8 is an enlarged sectional view of the tip unit detached from the handle unit of the probe component shown in FIG. 7.

Another probe embodiment is shown in FIGS. 7 and 8. Probe 150 includes reusable handpiece 152 and detachable tip unit 154. Handpiece 152 includes elongated tubular housing 156 that receives an assembly of operating cylinder 172, LVDT 168, accelerometer 170 that is connected to piston 172 in cylinder 174 by rod 176 that carries the core of LVDT 168, and slider block 184 that has socket 188 and four jaw chuck 186. A direct indication of motion of shaft 176 is provided over output wires 178 of the LVDT and a direct indication of acceleration is provided over output wires 180 of accelerometer 170 via cable sheath 182. Disc 160 at the end of cylinder 174 is seated on the end of housing 156 by threaded end cap 158, and fitting 162 receives air supply line 164.

Further details of the detachable probe tip unit 154 may be seen with reference to FIG. 8. Tip unit 154 includes plastic housing 190 that defines a through passage and has collar 192 at one end and sleeve portion 194 with snap coupling structure 196 at the other end. Disposed in housing 190 is probe drive assembly 200 that has a flange portion 202 that seats against shoulder 206. Tip 208 of coupling 206 is seated on the base of socket 188 and shoulder 210 is engaged by the jaws of chuck 186 to firmly secure coupling 206 to slide block 184. Extending forwardly from flange 202 is shaft portion 212 which is attached to spring coil 214 that is disposed withi contra-angle sheath tube 216 (that has an inner diameter of about one millimeter). Contra-angle portion 218 of sheath tube 216 is about two centimeters long. Disposed in tube portion 218 is probe tip member 212 that has enlarged tip 222. A taut nylon filament 224 extends through spring coil 214 between tip member 220 and shaft extension 212 and maintains the turns of coil 214 firmly seated against one another.

Another probe embodiment is shown in FIGS. 9-11. Probe unit 240 includes reuseable handpiece 242 and detachable tip unit 244 that is secured to handpiece 242 by clamp sleeve 245. Handpiece 242 includes tubular housing 246 in which is disposed operating cylinder 248 that houses the drive piston, and a reciprocating assembly of piston rod 250, core 252 of LVDT 254, and slider assembly 256. Slider assembly 256 houses accelerometer 258 at one end, has four jaw chuck 260 at its other end and includes body portion 262 on which is disposed outer sleeve 264 which has a groove 266 that receives key 268 to prevent rotation rotation of assembly 256. Intermediate transition sleeve member 270 of resilient material provides noise isolation. A direct indication of the motion of LVDT core 252 is provided over output wires 272, and a direct indication of acceleration is provided over output wires 274 from accelerometer 258. Hose barb 276 at the end of cylinder 248 receives air supply line 278. Cap 280 is threadedly received in handpiece housing 246 and carries coupling 282 that receives sheath 284 that protects the signal wires 272, 274 and air line 278.

The detachable probe tip unit 244 is designed for easy removal for cleaning and autoclaving, and includes housing 290, and bushing 292 that carry set screw 294 for securing contra-angle tip assembly 296. Further details of the probe tip unit 296 may be seen with reference to FIGS. 10 and 11. Tip assembly 296 includes outer stainless steel contra angle sheath sleeve 298 that has an outer diameter of about 1.1 millimeter and an inner diameter of about 0.8 millimeter; a guide tube 300 of stainless steel that has an outer diameter of about $\frac{1}{2}$ millimeter, an inner diameter of about $\frac{1}{4}$ millimeter and a length of about five centimeters with end 302 flared to a diameter of about 0.51 millimeter. Tube 300 is disposed within sleeve 298 with stabilizing transition sleeves 304, 306 supporting the two tubes 298, 300 in spaced aligned relation. The contra angle portion has a radius of about 0.6 centimeter and guide tube 300 has a length of about five centimeters and extends about one centimeter from the end of sheath 298.

Disposed in guide tube 300 is stainless steel probe wire 310 that has a diameter of about $\frac{1}{4}$ millimeter with an enlarged (laser formed) spherical tip 312 of about $\frac{1}{2}$ millimeter diameter. The flexibility of probe wire 310 in the contra angle area is enhanced by zones 314 (formed by selective etching) of reduced diameter (about $\frac{1}{8}$ millimeter) which extend throughout the contra angle area and which may be a single continuous zone of reduced diameter or may include spaced projections 316 of about two millimeters length in the reduced diameter zone 314. The end portions of wire 310 are of unreduced diameter, the end portion adjacent tip 312 having a length of about one centimeter. Secured to the end of probe wire 310 opposite tip 312 is coupling 318 (FIG. 9) which includes tip 320 that is received in chuck 260.

Operation of the probe 150 (240) is similar to operation of probe 12 described above. Tip 222 (302) of probe 150 (240) is positioned at the gingival margin and air pressure (three psi) is applied to piston 172 (250) to advance probe tip 222 (312) into the pocket to the pocket base. The piston 172 (250) and probe member 220 (310), interconnected by shafts 176 and 200 and coupling 184 in the FIG. 7 embodiment and by rod 250 and couplings 256 and 318 in the FIG. 9 embodiment, are retracted by application of negative pressure applied over line 164 (278). (A double acting cylinder arrangement may be alternatively used.) The travel of the probe tip 222 (312) is monitored by transducers 168, 170 (254, 258) and their outputs over lines 178, 180 (272, 274) to the associated data processor provide a direct measurement of probe tip displacement and the locations of the pocket base 114 and the cemento enamel junction 108. The flared tip 302 of guide tube 300 of the probe tip assembly of FIG. 9 may be used to manually locate the cemento-enamel junction (CEJ).

While particular embodiments of the invention has been shown and described, various modifications will be apparent to those skilled in the art, and therefore it is not intended that the invention be limited to the disclosed embodiments or to details thereof, and departures may be made therefrom within the spirit and scope of the invention.

What is claimed is:

1. Periodontal analysis apparatus comprising a handle component, a tip unit detachable from said handle component and defining a guide channel with a region of contra angle configuration, a probe member having a tip for insertion into a periodontal pocket of a patient, said probe member being disposed in said guide channel for reciprocating movement with the tip of said probe member extending outwardly from said channel, said probe member having flexibility such that said probe member may be reciprocated through said contra angle region and over a distance of about one centimeter in a probe insertion—retraction cycle of less than one second duration, force applying means in said handle component for producing reciprocating motion of said probe member along said channel, and transducer means in said handle component for monitoring probe motion perturbations and providing output signals indicative of probe member acceleration.

2. The apparatus of claim 1 wherein said force applying means generates a probe tip insertion force of less than one hundred grams and produces a reciprocating movement of said probe in said channel of less than two centimeters.

3. The apparatus of claim 1 wherein said probe member has an enlarged portion at its tip.

4. The apparatus of claim 3 wherein said probe member is a continuous metal wire member that has a diameter of less than 0.5 millimeter and has a series of spaced reduced diameter portions intermediate its ends.

5. The apparatus of claim 1 wherein said force applying means includes a piston member.

6. The apparatus of claim 1 wherein said channel defining tip unit is a metal tube that has a flared end adjacent the tip of said probe member.

7. The apparatus of claim 1 wherein said probe member has a coupling portion remote from said tip, and said force applying means includes a piston housed in said handle component and a rigid shaft that is driven by said piston and mechanically engages said coupling portion.

8. The apparatus of claim 1 wherein said detachable tip unit is sterilizable.

9. The apparatus of claim 1 and further including biasing means for biasing said probe member towards a retracted position, said biasing means producing a probe tip retraction force of about fifteen grams.

10. The apparatus of claim 1 wherein said probe member includes an elongated flexible assembly that includes a probe tip member, a coupling member, an elongated spring coil, and a tensioned filament extending through said spring coil from said probe tip member to said coupling member.

11. Periodontal analysis apparatus comprising a probe member having a tip for insertion into a periodontal pocket of a patient, a probe housing having a guide channel in which said probe member is disposed for reciprocating movement with the tip of said probe member extending outwardly from said channel, force applying means in said housing for producing reciprocating motion of said probe member along said channel, first transducer means for monitoring probe motion perturbations and providing output signals indicative thereof, second transducer means for monitoring displacement of said probe member from a reference position and providing output signals indicative thereof, and electronic signal processing means responsive to output signals from said first and second transducers for indicating attachment level—the distance of the cemento enamel junction from the base of the the periodontal pocket.

12. The apparatus of claim 11 wherein said second transducer is a linear variable differential transformer.

13. The apparatus of claim 12 wherein said force applying means includes a piston and an elongated member that extends through said linear variable differential transformer and is coupled to said probe member, said elongated member carrying the core of said linear variable differential transformer.

14. The apparatus of claim 11 wherein said first transducer is an accelerometer, said second transducer is a linear variable differential transformer and said force applying means includes a piston to which air from said source is applied, and further including an elongated portion coupled between said piston and said probe member and extending through said linear variable differential transformer, said elongated portion carrying the core of said linear variable differential transformer.

15. The apparatus of claim 14 wherein said probe member has an enlarged portion at its tip and further including probe member retracting means including a spring coupled to said probe member at a location remote from said tip, means coupling said piston to said probe member so that said spring biases said piston towards a retracted position, and said transducer means monitors the movement of said coupling means for providing information on pocket depth and CEJ location.

16. Periodontal analysis apparatus comprising a handle component, a sterilizable tip unit that defines a channel region of contra angle configuration, and that is detachable from said handle component, a probe member having a tip for insertion into a periodontal pocket of a patient, said probe member being disposed in said tip unit for reciprocating movement in said channel region with the tip of said probe member extending outwardly from said channel region, said probe member being an elongated solid metal wire member that has a diameter of less than 0.5 millimeter, and having a series of reduced diameter portions intermediate its ends that are disposed in said channel region, force applying means in said handle component for producing reciprocating motion of said probe member along said channel region, and transducer means in said handle component for monitoring probe motion perturbations and providing output signals indicative of probe member acceleration.

17. The apparatus of claim 16 wherein said channel defining tip unit is a metal tube that has a flared end adjacent the tip of said probe member.

18. The apparatus of claim 17 wherein said probe member has a coupling portion remote from said tip, and said force applying means includes a piston housed in said handle component and a rigid shaft that is driven by said piston and mechanically engages said coupling portion.

19. The apparatus of claim 16 wherein said elongated flexible probe member has an enlarged portion at its tip.

20. Periodontal analysis apparatus comprising a handle component, a sterilizable tip unit detachable from said handle component and defining a guide channel with a region of contra angle configuration, a probe member having a tip for insertion into a periodontal pocket of a patient, said probe member being disposed in said guide channel for reciprocating movement with the tip of said probe member extending outwardly from said channel, said probe member being an elongated solid metal wire member that has a diameter of less than 0.5 millimeter, and having a reduced diameter portion intermediate its ends that is disposed in said contra angle region, force applying means in said handle component that includes a source of air pressure for generating a probe insertion force of less than one hundred grams and producing reciprocating movement of said probe member along said channel in a probe insertion—retraction cycle of less than one second duration, transducer means in said handle component for monitoring probe motion perturbations and providing output signals indicative of probe member acceleration, a processor responsive to output signals of said transducer means, and output means responsive to said processor for providing data on the motion of said probe tip.

21. The apparatus of claim 20 wherein said source of air pressure is regulated and said force applying means includes a piston member to which air from said source is applied.

22. The apparatus of claim 20 wherein said probe member has a coupling portion remote from said tip, said force applying means includes a piston housed in said handle portion to which air from said source is applied, and said piston has a rigid shaft that engages said coupling portion.

23. A sterilizable detachable probe assembly for use with periodontal analysis apparatus that includes force applying means for producing reciprocating motion of a probe member and transducer means for monitoring probe motion and providing output signals idnicative thereof, said probe assembly including a probe member having a tip for insertion into a periodontal pocket of a patient, a housing of contra angle configuration having a guide channel in which said probe member is disposed for reciprocating movement with the tip of said probe member extending outwardly from said channel, said probe member having a reduced diameter portion intermediate its ends that is disposed in the region of contra angle configuration, and coupling structure for attaching said probe assembly to said periodontal analysis apparatus.

24. The assembly of claim 23 wherein said probe member is an elongated flexible member and has an enlarged portion at its tip.

25. The assembly of claim 23 wherein said contra angle region has a radius of about 0.6 centimeter.

26. The assembly of claim 23 wherein said guide channel defining structure is a metal tube that has a flared end adjacent the tip of said probe member.

27. The assembly of claim 23 wherein said probe member has a coupling portion remote from said tip, and said force applying means includes a rigid shaft that is driven by said force applying means and mechanically engages said probe member coupling portion.

28. The assembly of claim 23 wherein said probe member is a continuous metal wire member that has a diameter of less than 0.5 millimeter and said wire has, an enlarged portion at its tip.

29. Periodontal analysis apparatus comprising a probe member having a tip for insertion into a periodontal pocket of a patient, said probe member being a continuous metal wire member that has a diameter of less than 0.5 millimeter, an enlarged portion at its tip, and a reduced diameter portion intermediate its ends, a probe housing having a guide channel of contra angle configuration in which said probe member is disposed for reciprocating movement with the tip of said probe member extending outwardly from said channel, said reduced diameter portion of said metal wire member being disposed in the contra angle region of said guide channel, force applying means for generating a probe tip insertion force of less than one hundred grams and for producing reciprocating movement of said probe along said channel over a length of less than two centimeters, and transducer means for monitoring probe motion and providing output signals indicative thereof, said transducer means including a first transducer for providing output signals indicative of the acceleration of said probe member and a second transducer for monitoring displacement of said probe member from a reference position and providing output signals indicative thereof.

30. The apparatus of claim 29 wherein said probe housing includes a tip unit that defines said channel and is detachable from a handle component in which said transducer means is housed, and said channel defining tip unit is a metal tube that has a flared end adjacent the enlarged tip of said probe member.

* * * * *